US011410845B2

(12) United States Patent
Huang et al.

(10) Patent No.: US 11,410,845 B2
(45) Date of Patent: Aug. 9, 2022

(54) METHOD, APPARATUS AND SYSTEM FOR PROVIDING VOLTAGE SUPPLY FOR PHOTOIONIZATION DETECTOR LAMP

(71) Applicant: HONEYWELL INTERNATIONAL INC., Morris Plains, NJ (US)

(72) Inventors: Chuang Huang, Morris Plains, NJ (US); Tengfei Zhang, Morris Plains, NJ (US); Bing Chen, Morris Plains, NJ (US); Feng Liang, Morris Plains, NJ (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 258 days.

(21) Appl. No.: 16/881,712

(22) Filed: May 22, 2020

(65) Prior Publication Data

US 2020/0373147 A1    Nov. 26, 2020

(30) Foreign Application Priority Data

May 24, 2019  (CN) .......................... 201910438949.2

(51) Int. Cl.
*H01J 61/56* (2006.01)
*G01N 33/00* (2006.01)
*H02M 7/44* (2006.01)
*H02M 3/00* (2006.01)

(52) U.S. Cl.
CPC .......... *H01J 61/56* (2013.01); *G01N 33/0047* (2013.01); *G01N 2201/12* (2013.01); *H02M 3/00* (2013.01); *H02M 7/44* (2013.01)

(58) Field of Classification Search
CPC . H01J 61/56; G01N 33/0047; G01N 2201/12; G01N 27/64; H02M 3/00; H02M 7/44; H02M 7/48; G05F 1/44; G05F 1/575
See application file for complete search history.

(56) References Cited

U.S. PATENT DOCUMENTS

| 5,773,833 A | 6/1998 | Hsi |
| 2017/0201170 A1 | 7/2017 | Abu-Hajar |
| 2019/0075629 A1 | 3/2019 | Chitta et al. |

FOREIGN PATENT DOCUMENTS

| CA | 2216908 A1 * | 10/1996 | ........... H05B 41/282 |
| JP | H08-288083 A | 11/1996 | |
| WO | WO-2005052973 A2 * | 6/2005 | ......... H05B 41/2821 |

OTHER PUBLICATIONS

Combined Search and Examination Report issued in United Kingdom Application No. 2007733.5 dated Nov. 13, 2020, 5 pages.

* cited by examiner

*Primary Examiner* — David P Porta
*Assistant Examiner* — Fani Polyzos Boosalis
(74) *Attorney, Agent, or Firm* — Alston & Bird LLP

(57) ABSTRACT

Methods, apparatuses, and systems for providing an alternating current (AC) voltage supply for a photoionization detector lamp from a direct current (DC) voltage source are provided. An example apparatus may include a DC voltage to DC voltage (DC/DC) converter circuitry, and a feedback circuitry that is electronically coupled to the DC/DC converter circuitry and converts a reference AC voltage to a feedback DC voltage for the DC/DC converter circuitry. In some examples, the feedback circuitry may be electronically coupled to a DC voltage to AC voltage (DC/AC) converting circuitry to obtain the reference AC voltage.

20 Claims, 7 Drawing Sheets

METHOD, APPARATUS AND SYSTEM FOR PROVIDING VOLTAGE SUPPLY FOR PHOTOIONIZATION DETECTOR LAMP

CROSS-REFERENCE TO RELATED APPLICATIONS

This specification is based upon and claims the benefit of priority from Chinese patent application number CN 201910438949.2 filed on May 24, 2019, the entire contents of which are incorporated herein by reference.

FIELD OF THE INVENTION

The present disclosure relates generally to methods, apparatuses, and systems for providing a voltage supply, and more particularly, to methods, apparatuses, and systems for providing an alternating current (AC) voltage supply for a photoionization detector (PID) lamp.

BACKGROUND

A gas detector is a device that may detect and/or measure the concentration level of compounds in a gaseous substance, including, for example, organic compounds and inorganic compounds. For example, a photoionization detector (PID) is a gas detector that may measure the concentration level of volatile organic compounds in a gaseous substance. The term "volatile organic compound" (or "VOC") refers to organic compounds that may have a high vapor pressure at ordinary room temperature (i.e. they may easily become gases or vapors). Example chemicals in example volatile organic compounds may include, for example, formaldehyde, methane, and benzene.

A high level concentration of volatile organic compounds in indoor air or outdoor air may cause adverse effect on health and environment. As such, photoionization detectors may be utilized to measure and monitor the concentration level of volatile organic compounds in various indoor and/or outdoor locations.

Photoionization detectors may be installed within a portable device, which may be powered by a low direct current (DC) power source (such as, for example, a battery). However, many photoionization detectors may require a supply of a high alternating current (AC) power as a driving voltage for various components of the photoionization detectors. In this regard, existing methods and devices fail to overcome technical challenges associated with converting a low DC power to a high AC power for photoionization detectors.

BRIEF SUMMARY

Various embodiments described herein relate to methods, apparatuses, and systems for providing a voltage supply for a photoionization detector (PID) lamp. In particular, various embodiments are related to converting a low direct current (DC) voltage to a high alternating current (AC) voltage supply for powering the photoionization detector lamp.

In accordance with various embodiments of the present disclosure, an apparatus for providing a voltage supply for a photoionization detector lamp is provided. The apparatus comprises a DC voltage to DC voltage (DC/DC) converter circuitry and a feedback circuitry electronically coupled to the DC/DC converter circuitry and a DC voltage to AC voltage (DC/AC) converting circuitry.

In some examples, the DC/DC converter circuitry may comprise a DC/DC converter, and the DC/DC converter may be electronically coupled to a direct current (DC) voltage source and convert an input DC voltage from the DC voltage source to a compensated DC voltage based at least in part on a feedback DC voltage.

In some examples, the DC/AC converting circuitry may be electronically coupled to both the DC/DC converter circuitry and the photoionization detector lamp, and may convert the compensated DC voltage to the AC voltage supply for the photoionization detector lamp.

In some examples, the DC/AC converting circuitry may comprise an oscillating circuit and a transformer circuit electronically coupled to each other. In some examples, the oscillating circuit may be electronically coupled to the DC/DC converter. In some examples, the transformer circuit may be electronically coupled to the photoionization detector lamp.

In some examples, the transformer circuit of the DC/AC converting circuitry may comprise a primary winding and a secondary winding. In some examples, the secondary winding may comprise a transformer tap, and the reference voltage converting circuit may be electronically coupled to the transformer tap. In some examples, the transformer tap is positioned between 5% (inclusive) and 20% (inclusive) of the secondary winding of the transformer circuit. In some examples, the transformer tap is positioned at 6% of the secondary winding of the transformer circuit.

In some examples, the feedback circuitry may be electronically coupled to both the DC/DC converter circuitry and the DC/AC converting circuitry. In some examples, the feedback circuitry may obtain a reference AC voltage associated with the AC voltage supply, and may convert the reference AC voltage to the feedback DC voltage for the DC/DC converter.

In some examples, the feedback circuitry may comprise a reference voltage converting circuit and a reference voltage dividing circuit electronically coupled to each other.

In some examples, the reference voltage converting circuit may be electronically coupled to the transformer circuit. In some examples, the reference voltage converting circuit may convert the reference AC voltage to the reference DC voltage. In some examples, the reference voltage converting circuit may comprise a diode element and a capacitor element electronically coupled to each other. In some examples, the diode element may be electronically coupled to the transformer circuit. In some examples, the capacitor element may have an electrical capacitance between 1 nano-farad (inclusive) and 100 nano-farads (inclusive).

In some examples, the reference voltage dividing circuit may be electronically coupled to the DC/DC converter. In some examples, the reference voltage dividing circuit may convert the reference DC voltage to a feedback DC voltage and provide the feedback DC voltage to the DC/DC converter. In some examples, the reference voltage dividing circuit may comprise two resistor elements electronically coupled to each other. In some examples, each of the two resistor elements may have an electrical resistance between 100 kiloohms (inclusive) and 10 megaohms (inclusive).

In some examples, the feedback circuitry may comprise an amplifier element electronically coupled to the DC/DC converter. In some examples, the feedback circuitry may comprise a microcontroller unit electrically coupled to the DC/DC converter. In some examples, the system may comprise a switch circuitry electronically coupled to the DC/DC converter.

In accordance with various embodiments of the present disclosure, a system for providing an AC voltage supply for a photoionization detector lamp from a DC voltage source having an input DC voltage is provided. The system may comprise, for example, (1) a DC voltage to DC voltage (DC/DC) convertor circuitry, (2) a DC voltage to AC voltage (DC/AC) converting circuitry, and (3) a feedback circuitry.

In accordance with various embodiments of the present disclosure, a method for providing an alternating current (AC) voltage supply for a photoionization detector lamp from a direct current (DC) voltage source having an input DC voltage. The method comprises obtaining a reference AC voltage associated with a DC voltage to AC voltage (DC/AC) converting circuitry that is electronically coupled to the photoionization detector lamp, converting the reference AC voltage to a feedback DC voltage, converting the input DC voltage to a compensated DC voltage based at least in part on the feedback DC voltage, and causing a supply of the compensated DC voltage to the DC/AC converting circuitry.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
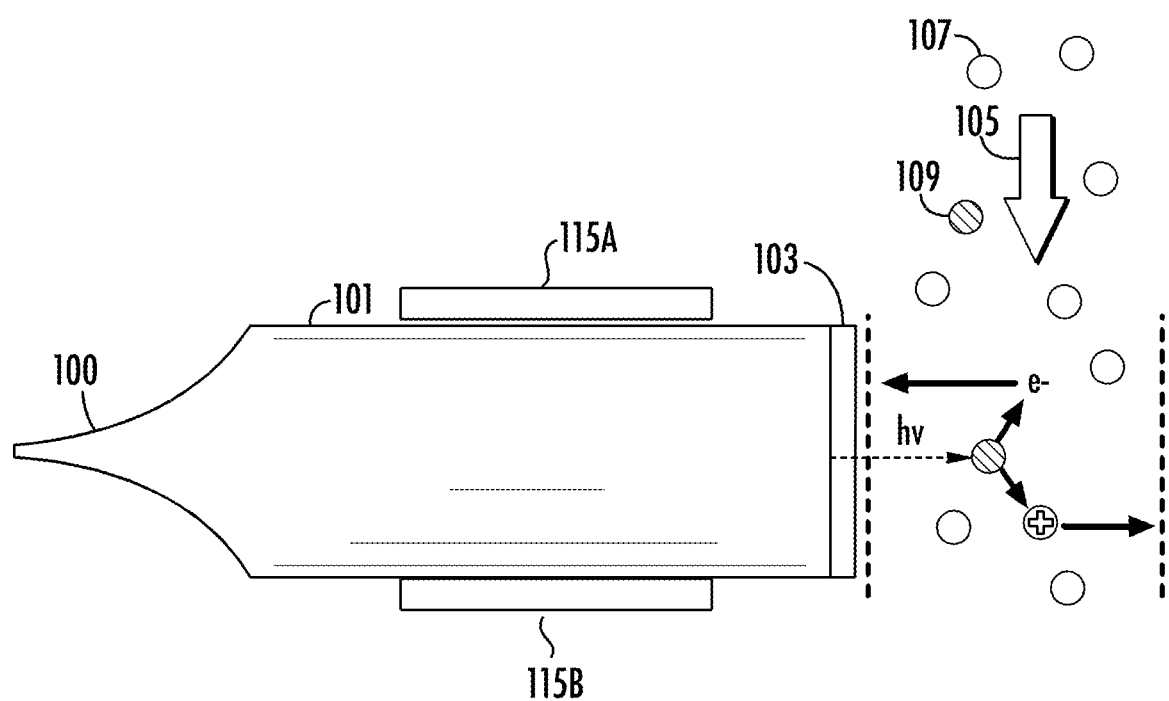
FIG. 1 illustrates an example schematic diagram showing an example photoionization detector lamp in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such component or feature may be optionally included in some embodiments, or it may be excluded.

The term "electronically coupled" in the present disclosure refers to two or more electrical elements (for example but not limited to, resistor element(s), capacitor element(s), inductor element(s), diode element(s)) and/or electric circuit (s) being connected through wired means (for example but not limited to, conductive wires or traces) and/or wireless means (for example but not limited to, electromagnetic field), such that energy (for example but not limited to electric current), data and/or information may be transmitted to and/or received from the electrical elements and/or electric circuit(s) that are electronically coupled.

As described above, technical challenges exist in converting a direct current (DC) voltage to an alternating current (AC) voltage for photoionization detector lamps. For example, a low DC voltage (for example but not limited to, 3.3 volts) may be supplied to a photoionization detector, while the photoionization detector lamp of the photoionization detector may require a high AC voltage (for example but not limited to, 1200 volts at peak-to-peak value) to properly function. In some examples, a photoionization detector may comprise a direct current to alternating current (DC/AC) converter circuit so as to perform the requisite conversion.

In some examples, the DC/AC converter circuit may comprise an oscillating circuit and a transformer circuit. In such examples, the oscillating circuit may convert an input DC voltage to an AC voltage, and the transformer circuit may convert the AC voltage from the oscillating circuit to a higher AC voltage for powering the photoionization detector lamp.

However, the accuracies of these conversions may be affected by a variety of factors. For example, temperature may affect the electrical properties (e.g. electrical conductivity, electrical resistance) of various components (e.g. resistor, capacitor, transformer, etc.) in the DC/AC converter circuit. Further, actual electrical properties of these components may fluctuate from marked electrical properties of these components within a percentage of error. These factors, compounded with characteristics of these conversions (e.g. high input current, high output frequency, high converting ratio), may cause the DC/AC converter circuit to output an erroneous AC driving voltage to the photoionization detector lamp. In other words, the actual, output AC voltage from the DC/AC converter circuit may drift from the calculated, desired output voltage for the photoionization detector lamp. This voltage drift may cause turn-on failures and reading errors of the photoionization detector lamp, and may further result in erroneous measurements by the photoionization detector.

In this regard, various example embodiments of the present disclosure may overcome these technical challenges associated with converting a direct current (DC) voltage to an alternating current (AC) voltage for photoionization detector lamps based on example embodiments that comprise DC voltage to DC voltage (DC/DC) converter circuitry, DC voltage to AC voltage (DC/AC) converting circuitry and/or feedback circuitry. In particular, some example embodiments of the present disclosure may reduce the risks of photoionization detector lamp turn-on failures and reading errors, and may compensate for factors that may affect voltage conversions as described above. Further, some example embodiments of the present disclosure may eliminate the need for separate power sources for the photoionization detector and the photoionization detector lamp, providing increased utilization and improved cost-efficiency.

Referring now to FIG. 1, an example schematic diagram showing an example photoionization detector lamp 100 in accordance with various embodiments of the present disclosure is provided. In particular, the example photoionization detector lamp 100 may comprise a glass tube member 101, and a window member 103.

In some examples, the glass tube member 101 may comprise a gaseous substance or a combination of gaseous substances, which may include, for example but not limited to, inert gases such as argon (Ar), xenon (Xe), and/or krypton (Kr). The gaseous substance(s) within the glass tube member 101 may be excited through any of a variety of excitation methods to produce an ultraviolet (UV) light source.

For example, a voltage (e.g. an alternating current (AC) voltage) may be supplied to the glass tube member 101 via, for example, a pair of electrodes 115A and 115B as shown in FIG. 1. In such examples, the AC voltage may cause ionization of the gaseous substance(s) within the glass tube member 101, resulting in a glow discharge. In particular, ions may travel alternately toward each of the electrode 115A and 115B, generating an electric current and forming a plasma. The glow discharge associated with the plasma may emit a low-wavelength ultraviolet (UV) light.

Referring back to FIG. 1, the ultraviolet light may be transmitted through the window member 103. In some examples, the window member 103 may comprise material (s) that enables and/or facilitates transmissions of low-wavelength ultraviolet light, including, for example, salt crystal materials. As the ultraviolet light passing through the window member 103, molecules in the gaseous substance that the photoionization detector are configured to detect may be exposed to the ultraviolet light.

As described above, the photoionization detector may be configured to detect, for example, volatile organic compound (VOC) in the air. In this regard, an anode element and a cathode element are provided. In some examples, the anode element may be an electrode that attracts negatively charged electrons. In some examples, the cathode element may be an electrode that attracts positively charged electrons.

As shown in FIG. 1, the air may flow through the photoionization detector in a direction as indicated by arrow 105. The air may comprise VOC molecules 109 and non-VOC molecules 107. As VOC molecules 109 and non-VOC molecules 107 passing through the photoionization detector, they may be exposed to the ultraviolet light generated by the photoionization detector lamp 100.

In particular, as shown in FIG. 1, the ultraviolet light may cause photoionization of the VOC molecules 109, which may result in electrons of the VOC molecules 109 being ejected and forming positively charged ions. The electrons may travel to the anode element, while the positively charged ions may travel to the cathode element. As the electrons and the positively charged ions being propelled to the corresponding electrodes, an electric current may be generated.

In contrast, the ultraviolet light may not cause photoionization of the non-VOC molecules 107, and the non-VOC molecules 107 do not generate electric current. In other words, the electric current generated through the ultraviolet light photoionization is proportional to the amount of VOC molecules 109 in the air. As such, the concentration level of the volatile organic compounds (VOC) may be determined by the photoionization detector based at least in part on the electric current.

As described above, the photoionization detector relies at least in part on the photoionization of the molecules caused by the ultraviolet light that is generated by the photoionization detector lamp. Therefore, providing a proper voltage supply for the photoionization detector lamp can be important for photoionization detector performance. However, many factors may affect the voltage supply for the photoionization detector lamp, resulting in an actual, output AC voltage that drifts from the calculated, desired output voltage, as described above.

Figure 2:
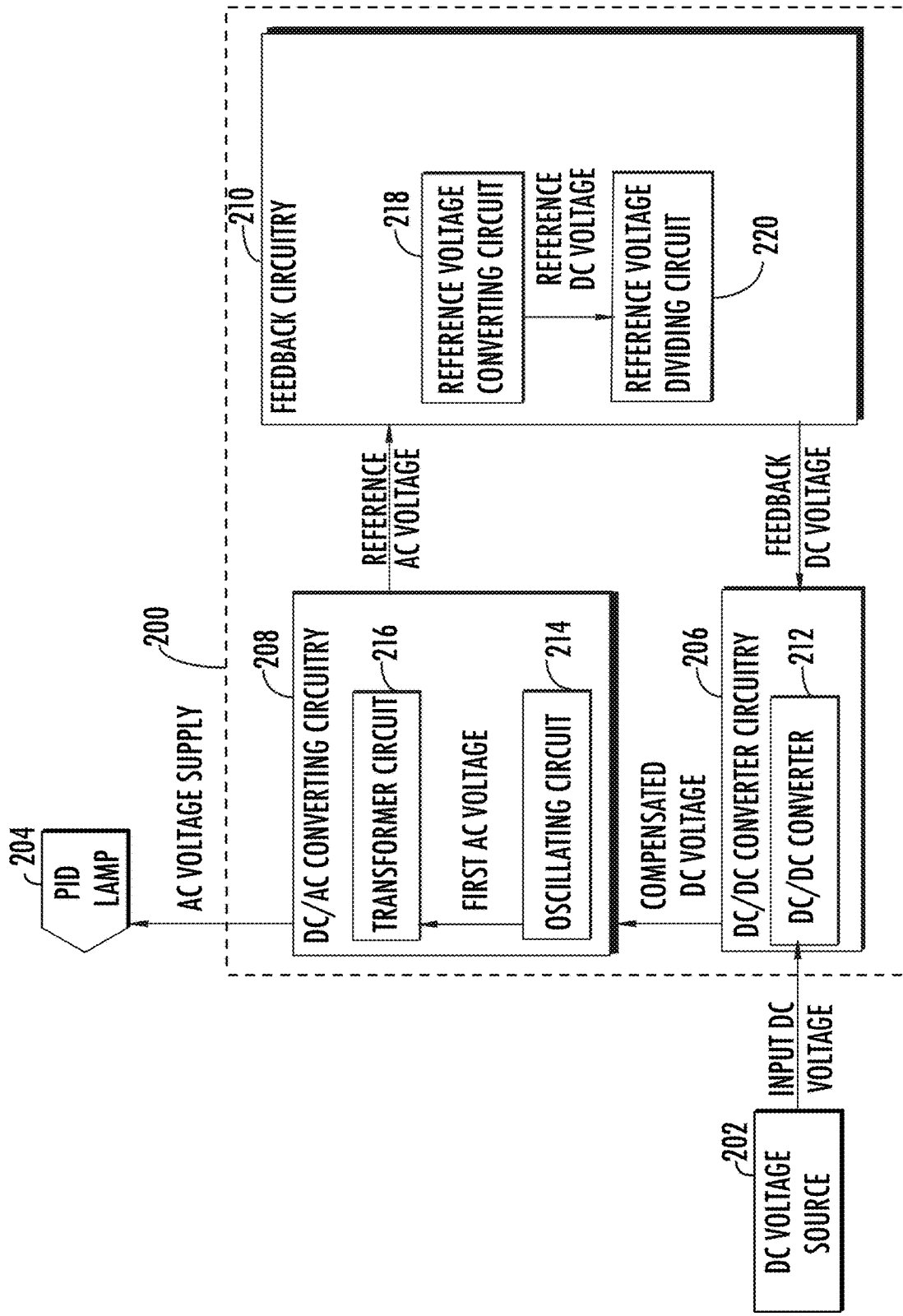
FIG. 2 illustrates an example block diagram of an example system in accordance with various embodiments of the present disclosure.

In this regard, various embodiments of the present disclosure may be embodied as systems and apparatuses for providing an alternating current (AC) voltage supply for a photoionization detector (PID) lamp. Referring now to FIG. 2, an example block diagram of various components of example systems and apparatuses in accordance with various embodiments of the present disclosure is shown.

As shown in FIG. 2, an example system 200 may comprise a DC voltage to DC voltage (DC/DC) converter circuitry 206, a DC voltage to AC voltage (DC/AC) converting circuitry 208, and a feedback circuitry 210. The DC/DC converter circuitry 206 may be electronically coupled to the DC/AC converting circuitry 208. The feedback circuitry 210 may be electronically coupled to both the DC/DC converter circuitry 206 and the DC/AC converting circuitry 208.

In some examples, the DC/DC converter circuitry 206 may comprise a DC/DC converter 212. The DC/DC converter 212 may be configured to convert one DC voltage to another. For example, the DC/DC converter 212 may be electronically coupled to a direct current (DC) voltage source 202. The DC voltage source 202 may provide an input DC voltage (for example but not limited to, 3.3 volts), and the DC/DC converter 212 may convert the input DC voltage to a compensated DC voltage based at least in part on a feedback DC voltage (provided by the feedback circuitry 210). Example structures of the DC/DC converter circuitry 206 are further illustrated and described below at least in connection with FIG. 3, FIG. 4, and FIG. 5.

In some examples, the DC/DC converter 212 may be electronically coupled to the DC/AC converting circuitry 208, and provide the compensated DC voltage to the DC/AC converting circuitry 208.

The DC/AC converting circuitry 208 may convert the compensated DC voltage to an AC voltage supply for powering the photoionization detector lamp 204. As shown in FIG. 2, the DC/AC converting circuitry 208 may comprise an oscillating circuit 214 and a transformer circuit 216. The oscillating circuit 214 and the transformer circuit 216 may be electronically coupled to each other.

In some examples, the oscillating circuit 214 is electronically coupled to the DC/DC converter 212 of the DC/DC converter circuitry 206, and may be configured to convert a DC voltage to an AC voltage. For example, the oscillating circuit 214 may receive the compensated DC voltage from the DC/DC converter 212, and may convert the compensated DC voltage to a first AC voltage. Example structures of the oscillating circuit 214 are further illustrated and described below at least in connection with FIG. 3, FIG. 4, and FIG. 5.

In some examples, the transformer circuit 216 is electronically coupled to the oscillating circuit 214, and may be configured to convert a low AC voltage to a high AC voltage. For example, the transformer circuit 216 may receive the first AC voltage from the oscillating circuit 214, and may convert the first AC voltage to a second AC voltage (i.e. the AC voltage supply for the photoionization detector lamp), where the second AC voltage may be higher than the first AC voltage. Further, the transformer circuit 216 may provide the second AC voltage as the AC voltage supply to power the photoionization detector lamp 204. Example structures of the transformer circuit 216 are further illustrated and described below at least in connection with FIG. 3, FIG. 4, and FIG. 5.

Referring back to FIG. 2, the feedback circuitry 210 may obtain a reference AC voltage associated with the AC voltage supply for the photoionization detector lamp 204, and may convert the reference AC voltage to a feedback DC voltage for the DC/DC converter circuitry 206. In some examples, the feedback circuitry 210 may comprise a reference voltage converting circuit 218 and a reference voltage dividing circuit 220. The reference voltage converting circuit 218 and a reference voltage dividing circuit 220 may be electronically coupled to each other.

In some examples, the reference voltage converting circuit 218 may be configured to convert an AC voltage to a DC voltage. For example, the reference voltage converting circuit 218 may be electronically coupled to the transformer circuit 216 of the DC/AC converting circuitry 208, and may convert the reference AC voltage to a reference DC voltage. Example structures of the reference voltage converting circuit 218 are further illustrated and described below at least in connection with FIG. 3, FIG. 4, and FIG. 5.

In some examples, the reference voltage dividing circuit 220 may be configured to convert a high DC voltage to a low DC voltage. For example, the reference voltage dividing circuit 220 may convert the reference DC voltage to a feedback DC voltage, and may provide the feedback DC voltage to the DC/DC converter 212 of the DC/DC converter circuitry 206. As described above, the DC/DC converter 212 may convert the input DC voltage to the compensated DC voltage based at least in part on the feedback DC voltage. Example structures of the reference voltage dividing circuit 220 are further illustrated and described below at least in connection with FIG. 3, FIG. 4, and FIG. 5.

While FIG. 2 illustrates the example system 200 as comprising the DC/DC converter circuitry 206, DC/AC converting circuitry 208, and the feedback circuitry 210, it is noted that example systems and apparatuses of the present disclosure may comprise fewer circuitry or more circuitry, without deviating from the scope of the present disclosure. For example, an example system may additionally include a switch circuitry that is configured to turn on/off the example system. As another example, an example apparatus may comprise the DC/DC converter circuitry 206 and the feedback circuitry 210, but not the DC/AC converting circuitry 208.

Figure 3:
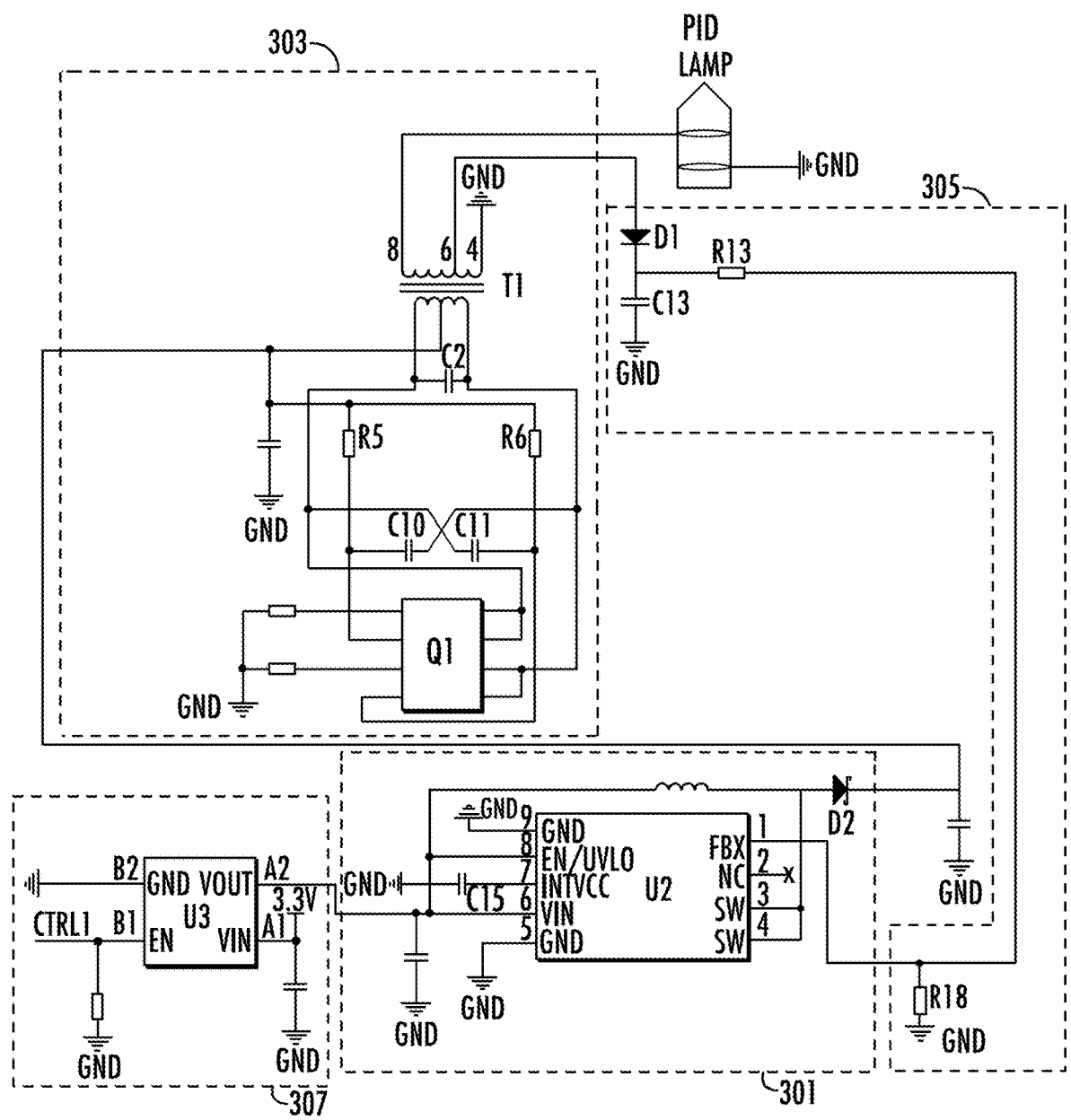
FIG. 3 illustrates an example circuit diagram in accordance with various embodiments of the present disclosure.
Figure 4:
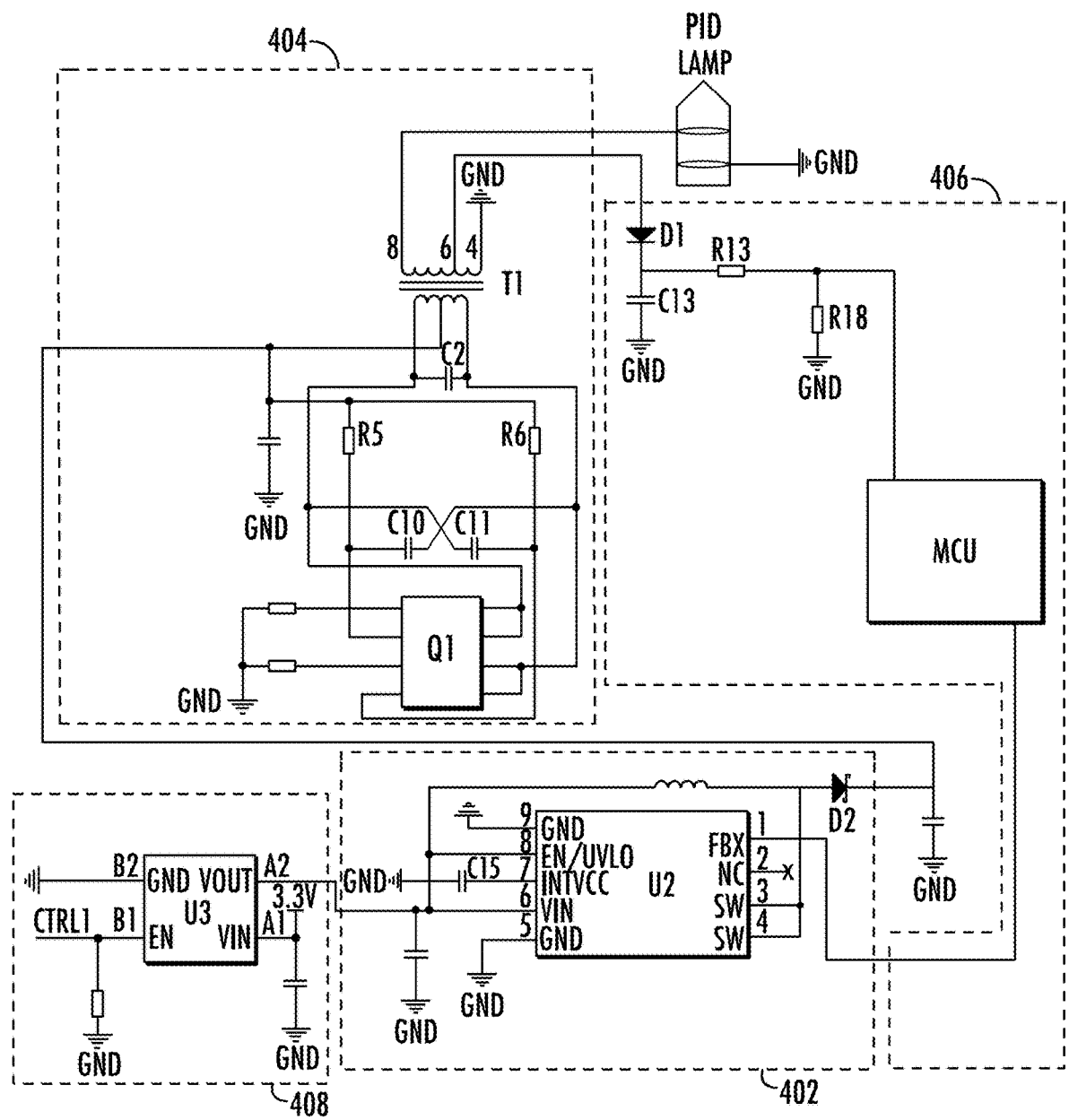
FIG. 4 illustrates an example circuit diagram in accordance with various embodiments of the present disclosure.
Figure 5:
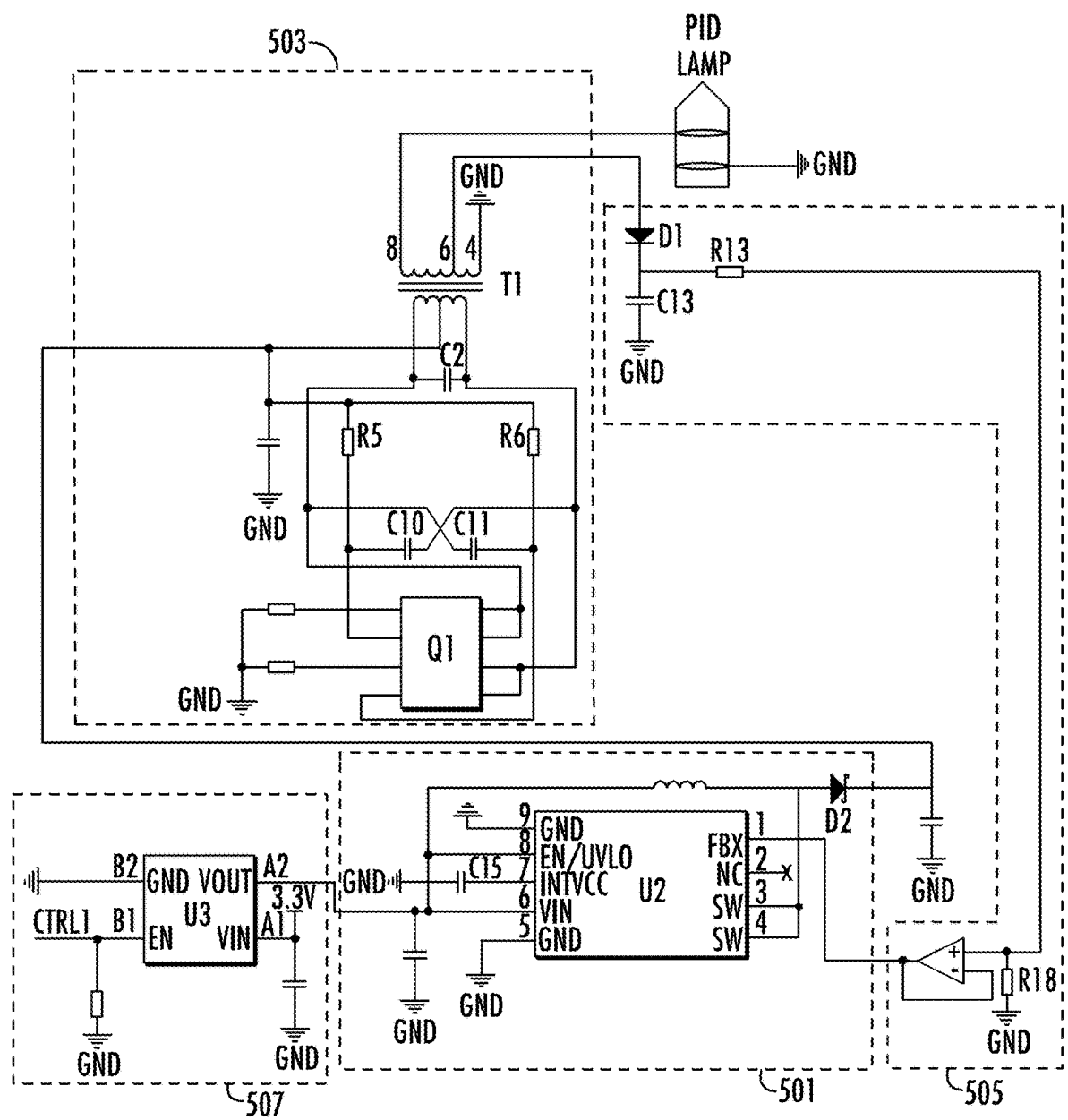
FIG. 5 illustrates an example circuit diagram in accordance with various embodiments of the present disclosure.

Referring now to FIG. 3, FIG. 4, and FIG. 5, various example circuit diagrams in accordance with various embodiments of the present disclosure are shown. In particular, FIG. 3, FIG. 4, and FIG. 5 may illustrate various example structures of example systems and apparatuses as described above.

FIG. 3 illustrates example structures of systems and apparatuses in accordance with the present disclosure. For example, an example system may comprise a switch circuitry 307, a DC/DC converter circuitry 301, a DC/AC converting circuitry 303, and a feedback circuitry 305.

In the embodiment as shown in FIG. 3, the switch circuitry 307 may comprise an integrated circuit (IC) switch (U3). The IC switch (U3) may comprise a VIN pin (A1), a VOUT pin (A2), an EN pin (B1), and a GND pin (B2). In some examples, the GND pin (B2) may be connected to the ground.

The VIN pin (A1) may receive an input DC voltage from a DC voltage source. For example, as shown in FIG. 3, the VIN pin (A1) may receive an input DC voltage of 3.3 volts. In some other examples, the input DC voltage may be of other values.

The EN pin (B1) may be configured to turn on or off the IC switch (U3) based on, for example, whether a control signal CTRL1 is received. When the IC switch (U3) is turned off, the VOUT pin (A2) of the IC switch (U3) may not provide a voltage to the DC/DC converter circuitry 301. When the IC switch (U3) is turned on, it may provide the input DC voltage to the DC/DC converter circuitry 301 via the VOUT pin (A2).

Referring back to FIG. 3, the input DC voltage may be received at a VIN pin (6) of the DC/DC converter (U2) of the DC/DC converter circuitry 301. The DC/DC converter (U2) may also receive a feedback DC voltage from the feedback circuitry 305 via an FBX pin (1) of the DC/DC converter (U2). Based on the input DC voltage and the feedback DC voltage, the DC/DC converter (U2) may provide a compensated voltage to the DC/AC converting circuitry 303, details of which are described below.

Further, in the embodiment as shown in FIG. 3, the DC/DC converter (U2) may comprise a pair of ground pins: a GND pin (5) and a GND pin (9), which may be connected to the ground. Additionally or alternatively, the DC/DC converter (U2) may comprise a pair of switch pins: a SW pin (3) and a SW pin (4), which may be connected to a Schottky diode (D2). Additionally or alternatively, the DC/DC converter (U2) may comprise a NC pin (2) that is not connected. Additionally or alternatively, the DC/DC converter (U2) may comprise an INTVCC pin (7) that is connected to the ground via a capacitor (C15) for internal voltage supply.

As described above, the DC/DC converter (U2) may provide a compensated DC voltage to the DC/AC converting circuitry 303. The DC/AC converting circuitry 303 may comprise an oscillating circuit and a transformer circuit. The oscillating circuit and the transformer circuit may be electronically coupled to each other.

The oscillating circuit of the DC/AC converting circuitry 303 may convert the compensated DC voltage to a first AC voltage. In the embodiment as shown in FIG. 3, the oscillating circuit may comprise electrical elements such as a switching transistor element (Q1), capacitor elements (C2), (C10) and (C11), and resistor elements (R5) and (R6), which are electronically coupled as shown in FIG. 3. In some examples, each of the capacitor elements (C10) and (C11) may have an electrical capacitance between 0.1 nano-farads (inclusive) and 10 nano-farads (inclusive). In some examples, the capacitor element (C2) may have an electrical capacitance between 1 nano-farad (inclusive) and 100 nano-farads (inclusive). In some examples, each of the resistor elements (R5) and (R6) may have an electrical resistance between 10 kiloohms (inclusive) and 100 kiloohms (inclusive).

The transformer circuit of the DC/AC converting circuitry 303 may convert the first AC voltage received from the oscillating circuit to a second AC voltage (i.e. the AC voltage supply for the photoionization detector lamp) that is higher than the first AC voltage. In the embodiment as shown in FIG. 3, the transformer circuit may comprise the transformer (T1) that is electronically coupled as shown in FIG. 3. The transformer (T1) may comprise a primary winding and a secondary winding. The primary winding may be electrically coupled to the oscillating circuit, and the secondary winding may be electronically coupled to the photoionization detector lamp to provide a voltage supply. Each of the primary winding and the secondary winding may comprise a metal coil having one or more turns.

As described above, various factors may affect the voltage supply to the photoionization detector lamp. For example, the voltage between the beginning turn (4) and the ending turn (8) of the secondary winding of the transformer (T1) may fluctuate due to changes in electrical properties of electrical elements caused by temperature increase. In this regard, various embodiments of the present disclosure may obtain a reference AC voltage from the secondary winding of the transformer (T1).

In the embodiment as shown in FIG. 3, the transformer (T1) may comprise a transformer tap (6) that is connected to the secondary winding and is positioned between the beginning turn (4) and the ending turn (8) of the secondary winding. The voltage between the beginning turn (4) and the transformer tap (6) is proportional to the voltage between the beginning turn (4) and the ending turn (8).

In other words, when the voltage supply to the photoionization detector lamp changes (i.e. the voltage between the beginning turn (4) and the ending turn (8) changes), the voltage between the beginning turn (4) and the transformer tap (6) also changes proportionally. As such, the voltage between the beginning turn (4) and the transformer tap (6) may be used as a reference AC voltage that reflects the actual change in the voltage supply to the photoionization detector lamp.

The transformer tap (6) may be positioned at a location between the beginning turn (4) and the ending turn (8) so that the reference AC voltage may fall within a suitable range for the feedback circuitry 305. In some examples, the transformer tap (6) is positioned between 5% (inclusive) and 20% (inclusive) of the secondary winding of the transformer (T1) (i.e. the voltage between the beginning turn (4) and the transformer tap (6) is between 5% (inclusive) and 20% (inclusive) of the voltage between the beginning turn (4) and the ending turn (8)).

In some examples, the transformer tap (6) is positioned at 6% of the secondary winding of the transformer (T1). In other words, the voltage between the beginning turn (4) and the transformer tap (6) is 6% of the voltage between the beginning turn (4) and the ending turn (8). For example, if the voltage between the beginning turn (4) and the ending turn (8) is 600 volts, the voltage between the beginning turn (4) and the transformer tap (6) may be 40 volts (which can be used as the reference AC voltage for the feedback circuitry 305).

As shown in FIG. 3, the feedback circuitry 305 is electronically coupled to the transformer tap (6) of the secondary winding and receives the reference AC voltage. The feedback circuitry 305 may comprise a reference voltage converting circuit and a reference voltage dividing circuit. The reference voltage converting circuit and the reference voltage dividing circuit may be electronically coupled to each other.

The reference voltage converting circuit of the feedback circuitry 305 may convert a reference AC voltage to a reference DC voltage. When the reference AC voltage changes, the converted reference DC voltage may change proportionally.

In the embodiment as shown in FIG. 3, the reference voltage converting circuit may comprise a diode element (D1) and a capacitor element (C13). The diode element (D1) and the capacitor element (C13) may be electronically coupled to each other. In particular, the diode element (D1) may be electronically coupled to the transformer tap (6) of the transformer (T1) in the DC/AC converting circuitry 303, and the capacitor element (C13) may be connected to the ground. In some examples, the capacitor element (C13) has an electrical capacitance between 1 nano-farad (inclusive) and 100 nano-farads (inclusive).

The reference voltage dividing circuit of the feedback circuitry 305 may convert the reference DC voltage to a corresponding feedback DC voltage that may be lower than the reference DC voltage. When the reference DC voltage changes, the converted feedback DC voltage may change proportionally.

In the embodiment as shown in FIG. 3, the reference voltage dividing circuit may comprise a resistor element (R13) and a resistor element (R18). The resistor element (R13) and the resistor element (R18) may be electronically coupled to each other. In particular, the resistor element (R13) may be electronically coupled between the diode element (D1) and the capacitor element (C13) of the reference voltage converting circuit, and the resistor element (R18) may be electronically coupled between the resistor element (R13) and the DC/DC converter (U2) of the DC/DC converter circuitry 301. In some examples, each of the resistor element (R13) and the resistor element (R18) may have an electrical resistance between 100 kiloohms (inclusive) and 10 megaohms (inclusive).

As shown in FIG. 3, the FBX pin (1) of the DC/DC converter (U2) may receive the feedback DC voltage from the feedback circuitry 305. As described above, the feedback DC voltage is converted by the feedback circuitry 305 based on a reference AC voltage from the DC/AC converting circuitry 303. When the reference AC voltage changes, the feedback DC voltage changes proportionally. As such, the feedback DC voltage received by the DC/DC converter (U2) reflects the actual change in the voltage supply to the photoionization detector lamp.

Based on the feedback DC voltage, the DC/DC converter (U2) may adjust the compensated voltage to DC/AC converting circuitry 303 accordingly. For example, when the feedback DC voltage is lower than a pre-determined value, the DC/DC converter (U2) may (gradually) increase the compensated voltage until the feedback DC voltage reaches the pre-determined value. When the feedback DC voltage is higher than a pre-determined value, the DC/DC converter (U2) may (gradually) decrease the compensated voltage until the feedback DC voltage drops to the pre-determined value. In some examples, when the feedback DC voltage is at the pre-determined value, it indicates that the corresponding AC voltage supply to the photoionization detector lamp is at the desired level.

While FIG. 3 illustrates that the DC/DC converter (U2) may adjust the compensated DC voltage through an under-voltage-lockout EN/UVLO pin (8), it is noted that scope of the present disclosure is not limited to the embodiment as shown in FIG. 3, and other suitable DC/DC converter may be implemented to adjust the compensated DC voltage based on the feedback DC voltage, without deviating from the scope of the present disclosure.

Referring now to FIG. 4, example structures of systems and apparatuses in accordance with the present disclosure are illustrated. For example, an example system may comprise a switch circuitry 408, a DC/DC converter circuitry 402, a DC/AC converting circuitry 404, and a feedback circuitry 406.

In some examples, the switch circuitry 408, the DC/DC converter circuitry 402, and the DC/AC converting circuitry 404 of FIG. 4 may be similar to the switch circuitry 307, the DC/DC converter circuitry 301, and the DC/AC converting circuitry 303 described above in connection with FIG. 3.

Further, the feedback circuitry 406 of FIG. 4 may comprise a reference voltage converting circuit and a reference voltage dividing circuit, which are similar to the reference voltage converting circuit and the reference voltage dividing circuit described above in connection with FIG. 3. The feedback circuitry 406 may further comprise a microcontroller unit (MCU) that is electronically coupled to the reference voltage dividing circuit and the DC/DC converter (U2) of the DC/DC converter circuitry 402.

In some examples, the microcontroller unit may be an integrated circuit that comprises a processing circuitry and a memory circuitry electronically coupled to each other. The memory circuitry may be a non-transitory memory that stores computer program instructions, and the computer program instructions may be executed by the processing circuitry.

In some examples, the microcontroller unit may perform various functions associated with the feedback circuitry 406. For example, the microcontroller unit may monitor the feedback DC voltage from the reference voltage dividing circuit, and may trigger a warning (such as an audio alarm through a speaker element that is connected to the processing circuitry) when the feedback DC voltage indicates that the photoionization detector lamp is powered by an insufficient or excessive voltage supply.

Referring now to FIG. 5, example structures of systems and apparatuses in accordance with the present disclosure are illustrated. For example, an example system may comprise a switch circuitry 507, a DC/DC converter circuitry 501, a DC/AC converting circuitry 503, and a feedback circuitry 505.

In some examples, the switch circuitry 507, the DC/DC converter circuitry 501, and the DC/AC converting circuitry 503 of FIG. 5 may be similar to the switch circuitry 307, the DC/DC converter circuitry 301, and the DC/AC converting circuitry 303 described above in connection with FIG. 3.

Further, the feedback circuitry 505 of FIG. 5 may comprise a reference voltage converting circuit and a reference voltage dividing circuit, which are similar to the reference voltage converting circuit and the reference voltage dividing circuit described above in connection with FIG. 3. The feedback circuitry 505 may further comprise an amplifier element that is electronically coupled to the reference voltage dividing circuit and the DC/DC converter (U2) of the DC/DC converter circuitry 501. In the embodiment as shown in FIG. 5, the amplifier element may be a closed-loop amplifier, which may, for example, provide a more constant feedback DC voltage to the DC/DC converter (U2) of the DC/DC converter circuitry.

Referring now to FIG. 6, FIG. 7, FIG. 8, and FIG. 9, various example alternating current (AC) waveform diagrams showing circuit output voltages are provided. In particular, the same input voltage is provided to the circuits of FIG. 6, FIG. 7, FIG. 8, and FIG. 9.

Figure 6:
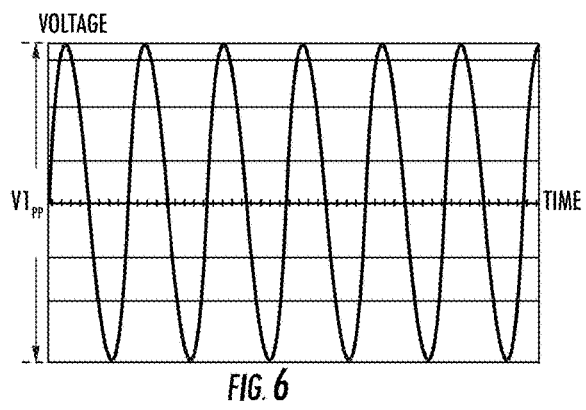
FIG. 6 illustrates an example alternating current (AC) waveform diagram in accordance with various embodiments of the present disclosure.
Figure 7:
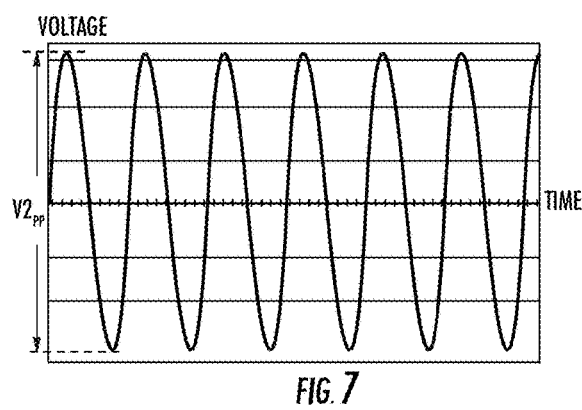
FIG. 7 illustrates an example AC waveform diagram in accordance with various embodiments of the present disclosure.

FIG. 6 and FIG. 7 illustrate the AC waveforms of a circuit that does not implement embodiments of the present disclosure. In FIG. 6, no photoionization detector lamp is connected to the circuit; in FIG. 7, a photoionization detector lamp is connected to the circuit. In some examples, the peak-to-peak voltage $V1_{pp}$ in FIG. 6 may be 1.30 kilovolts, and the peak-to-peak voltage $V2_{pp}$ in FIG. 7 may be 1.20 kilovolts. In other words, the photoionization detector lamp may cause a 7% voltage drift in a circuit that does not implement embodiments of the present disclosure.

Figure 8:
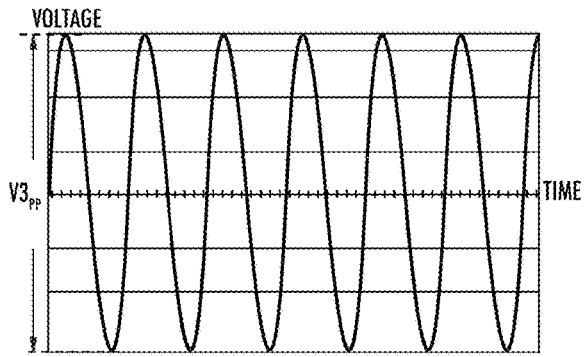
FIG. 8 illustrates an example AC waveform diagram in accordance with various embodiments of the present disclosure.
Figure 9:
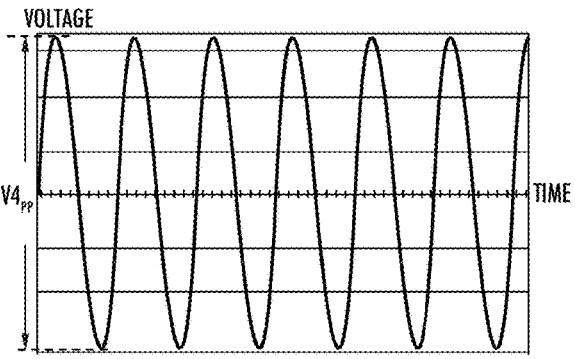
FIG. 9 illustrates an example AC waveform diagram in accordance with various embodiments of the present disclosure.

FIG. 8 and FIG. 9 illustrate the AC waveforms of a circuit that implements example embodiments of the present disclosure. In FIG. 8, no photoionization detector lamp is connected to the circuit; in FIG. 9, a photoionization detector lamp is connected to the circuit. In some examples, the peak-to-peak voltage $V3_{pp}$ in FIG. 8 may be 1.31 kilovolts, and the peak-to-peak voltage $V4_{pp}$ in FIG. 9 may be 1.30 kilovolts. In other words, the photoionization detector lamp may cause less than a 1% voltage drift in a circuit that implements embodiments of the present disclosure.

Comparing the peak-to-peak voltage difference between FIGS. 6-7 and the peak-to-peak voltage difference between FIGS. 8-9, it is noted that various embodiments of the present disclosure may reduce the voltage drift in providing voltage supply to a photoionization detector lamp.

Various embodiments of the present disclosure may be embodied as methods for providing an alternating current (AC) voltage supply for a photoionization detector (PID) lamp. In this regard, FIG. 10 depicts a flow diagram illustrating an example method in accordance with various embodiments of the present disclosure.

In some examples, each block of the flow diagram, and combinations of blocks in the flow diagram, may be implemented by various means such as hardware, firmware, circuitry and/or other devices associated with execution of software including one or more computer program instructions.

Figure 10:
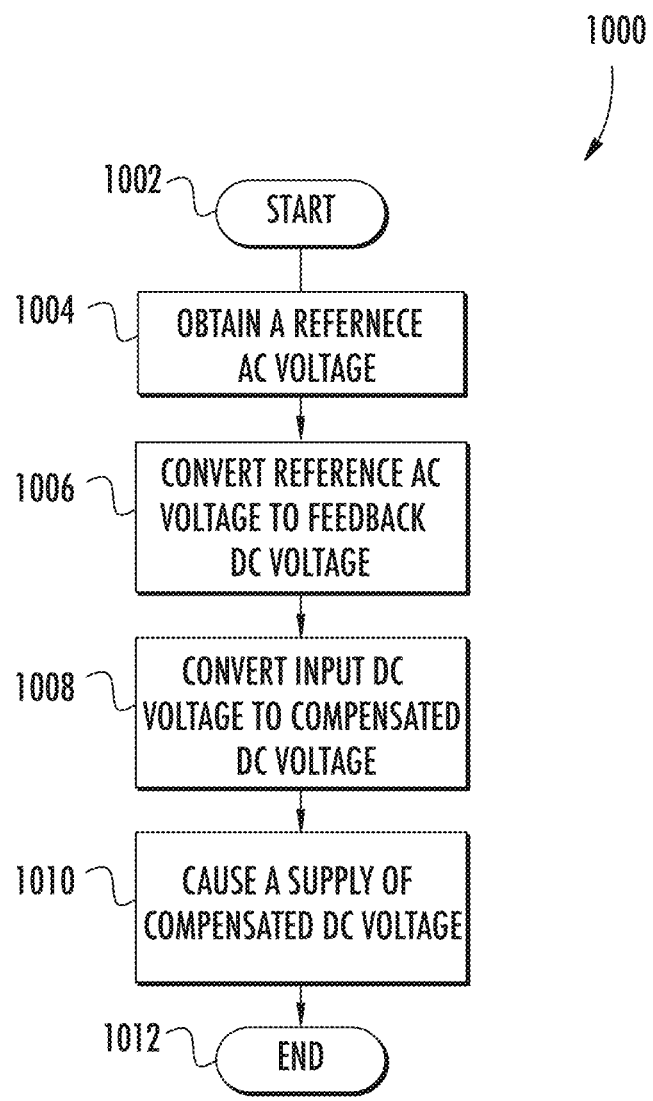
FIG. 10 illustrates an example flow diagram illustrating an example method in accordance with various embodiments of the present disclosure.

In some examples, one or more of the procedures described in FIG. 10 may be embodied by computer program instructions, which may be stored by a memory circuitry (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flow diagram block(s). Further, the system may comprise one or more other circuitries, such as, for example, the DC/DC converter circuitry, the DC/AC converting circuitry, and the feedback circuitry described above in connection with FIG. 2, FIG. 3, FIG. 4, and FIG. 5. Various circuitries of the system may be electronically coupled between and/or among each other to transmit and/or receive energy, data and/or information.

In some examples, embodiments may take the form of a computer program product on a non-transitory computer-readable storage medium storing computer-readable program instructions (e.g. computer software). Any suitable computer-readable storage medium may be utilized, including non-transitory hard disks, CD-ROMs, flash memory, optical storage devices, or magnetic storage devices.

Referring now to FIG. 10, an example method 1000 in accordance with some embodiments of the present disclosure is illustrated. The method 1000 starts at block 1002.

At block 1004, a feedback circuitry of an example apparatus (such as, for example, the feedback circuitry 210, the feedback circuitry 305, the feedback circuitry 406, and the feedback circuitry 505 described above in connection with FIG. 2, FIG. 3, FIG. 4, and FIG. 5, respectively) may obtain a reference alternating current (AC) voltage associated with the photoionization detector lamp. For example, the feedback circuitry may obtain the reference AC voltage from a DC voltage to AC voltage (DC/AC) converting circuitry that is electronically coupled to the photoionization detector lamp.

In some examples, the DC/AC converting circuitry may comprise a transformer that provides an AC voltage supply to the photoionization detector lamp through a secondary winding. In such examples, the reference AC voltage may be a lower voltage than the AC voltage supply, and the reference AC voltage may change proportionally as the AC voltage supply changes.

At block 1006, a feedback circuitry of an example apparatus (such as, for example, the feedback circuitry 210, the feedback circuitry 305, the feedback circuitry 406, and the feedback circuitry 505 described above in connection with FIG. 2, FIG. 3, FIG. 4, and FIG. 5, respectively) may convert the reference AC voltage to a feedback direct current (DC) voltage.

In some examples, the feedback circuitry may convert the reference AC voltage to the feedback DC voltage via a reference voltage converting circuit and a reference voltage dividing circuit, as described above. In some examples, the feedback DC voltage may change proportionally as the reference AC voltage changes.

At block 1008, a DC voltage to DC voltage (DC/DC) converter circuitry of an example apparatus (such as, for example, the DC/DC converter circuitry 206, the DC/DC converter circuitry 301, the DC/DC converter circuitry 402, and the DC/DC converter circuitry 501 described above in connection with FIG. 2, FIG. 3, FIG. 4, and FIG. 5, respectively) may convert the input DC voltage to a compensated DC voltage based at least in part on the feedback DC voltage.

In some examples, when the feedback DC voltage is lower than a pre-determined value, the DC/DC converter may (gradually) increase the compensated voltage until the feedback DC voltage reaches the pre-determined value. In some examples, when the feedback DC voltage is higher than a pre-determined value, the DC/DC converter (U2) may (gradually) decrease the compensated voltage until the feedback DC voltage drops to the pre-determined value.

At block 1010, a DC/DC converter circuitry of an example apparatus (such as, for example, the DC/DC converter circuitry 206, the DC/DC converter circuitry 301, the DC/DC converter circuitry 402, and the DC/DC converter circuitry 501 described above in connection with FIG. 2, FIG. 3, FIG. 4, and FIG. 5, respectively) may cause a supply of the compensated DC voltage to the DC/AC converting circuitry. In some examples, the DC/AC converting circuitry may convert the compensated DC voltage to an AC voltage supply for the photoionization detector lamp.

The method 1000 ends at block 1012.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. An apparatus for providing a voltage supply for a photoionization detector lamp, the apparatus comprising:
   a DC voltage to DC voltage (DC/DC) converter circuitry comprising a DC/DC converter, wherein the DC/DC converter is electronically coupled to a direct current (DC) voltage source and converts an input DC voltage from the DC voltage source to a compensated DC voltage based at least in part on a feedback DC voltage; and
   a feedback circuitry electronically coupled to the DC/DC converter circuitry and a DC voltage to AC voltage (DC/AC) converting circuitry, wherein the feedback circuitry obtains a reference alternating current (AC) voltage associated with the DC/AC converting circuitry and converts the reference AC voltage to the feedback DC voltage for the DC/DC converter.

2. The apparatus of claim 1, wherein the DC/AC converting circuitry comprises an oscillating circuit and a transformer circuit electronically coupled to each other, wherein the oscillating circuit is electronically coupled to the DC/DC converter, wherein the transformer circuit is electronically coupled to the photoionization detector lamp.

3. The apparatus of claim 2, wherein the feedback circuitry comprises a reference voltage converting circuit and a reference voltage dividing circuit electronically coupled to each other, wherein the reference voltage converting circuit is electronically coupled to the transformer circuit, wherein the reference voltage dividing circuit is electronically coupled to the DC/DC converter.

4. The apparatus of claim 3, wherein the reference voltage converting circuit converts the reference AC voltage to a reference DC voltage, wherein the reference voltage dividing circuit converts the reference DC voltage to the feedback DC voltage and provides the feedback DC voltage to the DC/DC converter.

5. The apparatus of claim 3, wherein the transformer circuit comprises a primary winding and a secondary winding, wherein the secondary winding comprises a transformer tap, wherein the reference voltage converting circuit is electronically coupled to the transformer tap.

6. The apparatus of claim 5, wherein the transformer tap is positioned between 5% (inclusive) and 20% (inclusive) of the secondary winding of the transformer circuit.

7. The apparatus of claim 6, wherein the transformer tap is positioned at 6% of the secondary winding of the transformer circuit.

8. The apparatus of claim 3, wherein the reference voltage converting circuit comprises a diode element and a capacitor element electronically coupled to each other, wherein the diode element is electronically coupled to the transformer circuit.

9. The apparatus of claim 8, wherein the capacitor element has an electrical capacitance between 1 nano-farad (inclusive) and 100 nano-farads (inclusive).

10. The apparatus of claim 3, wherein the reference voltage dividing circuit comprises two resistor elements electronically coupled to each other.

11. The apparatus of claim 10, wherein each of the two resistor elements has an electrical resistance between 100 kiloohms (inclusive) and 10 megaohms (inclusive).

12. The apparatus of claim 1, further comprising a switch circuitry electronically coupled to the DC/DC converter.

13. The apparatus of claim 1, wherein the feedback circuitry comprises a microcontroller unit electrically coupled to the DC/DC converter.

14. The apparatus of claim 1, wherein the feedback circuitry comprises an amplifier element electronically coupled to the DC/DC converter.

15. A system for providing an alternating current (AC) voltage supply for a photoionization detector lamp from a direct current (DC) voltage source having an input DC voltage, the system comprising:
- a DC voltage to DC voltage (DC/DC) converter circuitry comprising a DC/DC converter, wherein the DC/DC converter is electronically coupled to the DC voltage source and converts the input DC voltage to a compensated DC voltage based at least in part on a feedback DC voltage;
- a DC voltage to AC voltage (DC/AC) converting circuitry electronically coupled to the DC/DC converter circuitry and the photoionization detector lamp, wherein the DC/AC converting circuitry converts the compensated DC voltage to the AC voltage supply for the photoionization detector lamp; and
- a feedback circuitry electronically coupled to the DC/DC converter circuitry and the DC/AC converting circuitry, wherein the feedback circuitry obtains a reference AC voltage associated with the AC voltage supply and converts the reference AC voltage to the feedback DC voltage for the DC/DC converter.

16. The system of claim 15, wherein the DC/AC converting circuitry comprises an oscillating circuit and a transformer circuit electronically coupled to each other, wherein the oscillating circuit is electronically coupled to the DC/DC converter, wherein the transformer circuit is electronically coupled to the photoionization detector lamp.

17. The system of claim 16, wherein the feedback circuitry comprises a reference voltage converting circuit and a reference voltage dividing circuit electronically coupled to each other, wherein the reference voltage converting circuit is electronically coupled to the transformer circuit, wherein the reference voltage dividing circuit is electronically coupled to the DC/DC converter.

18. The system of claim 17, wherein the reference voltage converting circuit converts the reference AC voltage to a reference DC voltage, wherein the reference voltage dividing circuit converts the reference DC voltage to the feedback DC voltage and provides the feedback DC voltage to the DC/DC converter.

19. The system of claim 17, wherein the transformer circuit comprises a primary winding and a secondary winding, wherein the secondary winding comprises a transformer tap, wherein the reference voltage converting circuit is electronically coupled to the transformer tap.

20. A method for providing an alternating current (AC) voltage supply for a photoionization detector lamp from a direct current (DC) voltage source having an input DC voltage, the method comprising:
- obtaining a reference AC voltage associated with a DC voltage to AC voltage (DC/AC) converting circuitry that is electronically coupled to the photoionization detector lamp;
- converting the reference AC voltage to a feedback DC voltage;
- converting the input DC voltage to a compensated DC voltage based at least in part on the feedback DC voltage; and
- causing a supply of the compensated DC voltage to the DC/AC converting circuitry.

* * * * *